(12) United States Patent
Dogdas et al.

(10) Patent No.: US 11,107,573 B2
(45) Date of Patent: Aug. 31, 2021

(54) SYSTEMS AND METHODS FOR PROCESSING ELECTRONIC IMAGES FOR GENERALIZED DISEASE DETECTION

(71) Applicant: PAIGE.AI, Inc., New York, NY (US)

(72) Inventors: Belma Dogdas, Ridgewood, NJ (US); Christopher Kanan, Rochester, NY (US); Thomas Fuchs, New York, NY (US); Leo Grady, Darien, CT (US)

(73) Assignee: PAIGE.AI, INC., New York, NY (US)

( * ) Notice: Subject to any disclaimer, the term of this patent is extended or adjusted under 35 U.S.C. 154(b) by 0 days.

(21) Appl. No.: 17/126,865

(22) Filed: Dec. 18, 2020

(65) Prior Publication Data

US 2021/0210195 A1      Jul. 8, 2021

Related U.S. Application Data

(60) Provisional application No. 62/956,876, filed on Jan. 3, 2020.

(51) Int. Cl.
  *G16H 30/40*   (2018.01)
  *G16H 50/20*   (2018.01)
  *G06T 7/00*    (2017.01)

(52) U.S. Cl.
  CPC ........... *G16H 30/40* (2018.01); *G06T 7/0012* (2013.01); *G16H 50/20* (2018.01);
  (Continued)

(58) Field of Classification Search
  CPC ...... G16H 30/40; G16H 50/20; G06T 7/0012; G06T 2207/20081; G06T 2207/30024; G06T 2207/30096
  See application file for complete search history.

(56) References Cited

U.S. PATENT DOCUMENTS

2017/0007187 A1*  1/2017  Breneisen ............ A61B 5/0075
2019/0073569 A1*  3/2019  Ben-Ari ................. G16H 50/20
(Continued)

FOREIGN PATENT DOCUMENTS

WO       2017055412 A1     4/2017

OTHER PUBLICATIONS

International Search Report and Written Opinion in International Application No. PCT/US2020/066045, dated Mar. 24, 2021 (14 pages).
(Continued)

*Primary Examiner* — Nay A Maung
*Assistant Examiner* — Jose M Torres
(74) *Attorney, Agent, or Firm* — Bookoff McAndrews, PLLC

(57) ABSTRACT

Systems and methods are disclosed for generating a specialized machine learning model by receiving a generalized machine learning model generated by processing a plurality of first training images to predict at least one cancer characteristic, receiving a plurality of second training images, the first training images and the second training images include images of tissue specimens and/or images algorithmically generated to replicate tissue specimens, receiving a plurality of target specialized attributes related to a respective second training image of the plurality of second training images, generating a specialized machine learning model by modifying the generalized machine learning model based on the plurality of second training images and the target specialized attributes, receiving a target image corresponding to a target specimen, applying the specialized machine learning model to the target image to determine at least one characteristic of the target image, and outputting the characteristic of the target image.

20 Claims, 9 Drawing Sheets

(52) U.S. Cl.
CPC .............. *G06T 2207/20081* (2013.01); *G06T 2207/30024* (2013.01); *G06T 2207/30096* (2013.01)

(56) References Cited

U.S. PATENT DOCUMENTS

| | | | |
|---|---|---|---|
| 2019/0156159 A1 | 5/2019 | Kopparapu | |
| 2019/0347557 A1* | 11/2019 | Khan | G06N 3/084 |
| 2019/0355114 A1* | 11/2019 | Muehlberg | G06T 7/11 |
| 2019/0370965 A1* | 12/2019 | Lay | G06N 20/00 |
| 2020/0160032 A1* | 5/2020 | Allen | G06N 3/0454 |
| 2020/0210767 A1* | 7/2020 | Do | G06N 3/08 |
| 2020/0225811 A1* | 7/2020 | Sieniek | G06F 3/04883 |
| 2020/0272864 A1* | 8/2020 | Faust | G06K 9/3233 |
| 2020/0372636 A1* | 11/2020 | Ha | G06T 3/40 |
| 2020/0388028 A1* | 12/2020 | Agus | G16H 50/20 |

OTHER PUBLICATIONS

H. Shin et al. "Deep Convolutional Neural Networks for Computer-Aided Detection: CNN Architectures, Dataset Characteristics and Transfer Learning," in IEEE Transactions on Medical Imaging, vol. 35, No. 5, pp. 1285-1298, May 2016, doi: 10.1109/TMI.2016.2528162.

* cited by examiner

SYSTEMS AND METHODS FOR PROCESSING ELECTRONIC IMAGES FOR GENERALIZED DISEASE DETECTION

RELATED APPLICATION(S)

This application claims priority to U.S. Provisional Application No. 62/956,876 filed Jan. 3, 2020, the entire disclosure of which is hereby incorporated herein by reference in its entirety.

FIELD OF THE DISCLOSURE

Various embodiments of the present disclosure relate generally to image-based specimen classification and related image processing methods. More specifically, particular embodiments of the present disclosure relate to systems and methods for processing images to develop a generalized pan-cancer machine learning model for development of biomarkers in clinical and pre-clinical studies.

BACKGROUND

In oncology studies, it is increasingly important to stratify different patient groups to develop personalized therapeutic strategies, to measure tumor progression, and/or to evaluate efficacy of therapies. The current practice for such stratification is to use clinical trial samples that are relatively small compared to the needs of most machine learning systems. For example, many Phase III clinical trials enroll fewer than 5000 patients and Phase I and Phase II clinical trials enroll even lesser patients (e.g., Phase 1 generally enrolls less than 100 patients, Phase 2 generally enrolls less than 300 patients). Using deep learning and many other end-to-end machine learning techniques with these small datasets is challenging due to overfitting, which results in the model making inaccurate predictions.

Accordingly, it would be beneficial to apply machine learning technology for deep learning and other end-to-end machine learning techniques with small datasets such as those provided via clinical trials.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for identifying or verifying specimen type or specimen properties from image analysis of tissue specimens.

A method for generating a specialized machine learning model includes receiving a generalized machine learning model generated by processing a plurality of first training images to predict at least one cancer characteristic; receiving a plurality of second training images, wherein the first training images and the second training images comprise images of tissue specimens and/or images algorithmically generated to replicate tissue specimens; receiving a plurality of target specialized attributes each related to a respective second training image of the plurality of second training images; generating a specialized machine learning model by modifying the generalized machine learning model based on the plurality of second training images and the respective target specialized attributes; receiving a target image corresponding to a target specimen; applying the specialized machine learning model to the target image to determine at least one characteristic of the target image; and outputting the at least one characteristic of the target image.

A system for generating a specialized machine learning model includes a memory storing instructions; and a processor executing the instructions to perform a process including receiving a generalized machine learning model generated by processing a plurality of first training images to predict at least one cancer characteristic; receiving a plurality of second training images, wherein the first training images and the second training images comprise images of tissue specimens and/or images algorithmically generated to replicate tissue specimens; receiving a plurality of target specialized attributes each related to a respective second training image of the plurality of second training images; generating a specialized machine learning model by modifying the generalized machine learning model based on the plurality of second training images and the respective target specialized attributes; receiving a target image corresponding to a target specimen; applying the specialized machine learning model to the target image to determine at least one characteristic of the target image; and outputting the at least one characteristic of the target image.

A non-transitory computer-readable medium storing instructions that, when executed by processor, cause the processor to perform a method for generating a specialized machine learning model, the method includes receiving a generalized machine learning model generated by processing a plurality of first training images to predict at least one cancer characteristic; receiving a plurality of second training images, wherein the first training images and the second training images comprise images of tissue specimens and/or images algorithmically generated to replicate tissue specimens; receiving a plurality of target specialized attributes each related to a respective second training image of the plurality of second training images; generating a specialized machine learning model by modifying the generalized machine learning model based on the plurality of second training images and the respective target specialized attributes; receiving a target image corresponding to a target specimen; applying the specialized machine learning model to the target image to determine at least one characteristic of the target image; and outputting the at least one characteristic of the target image. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
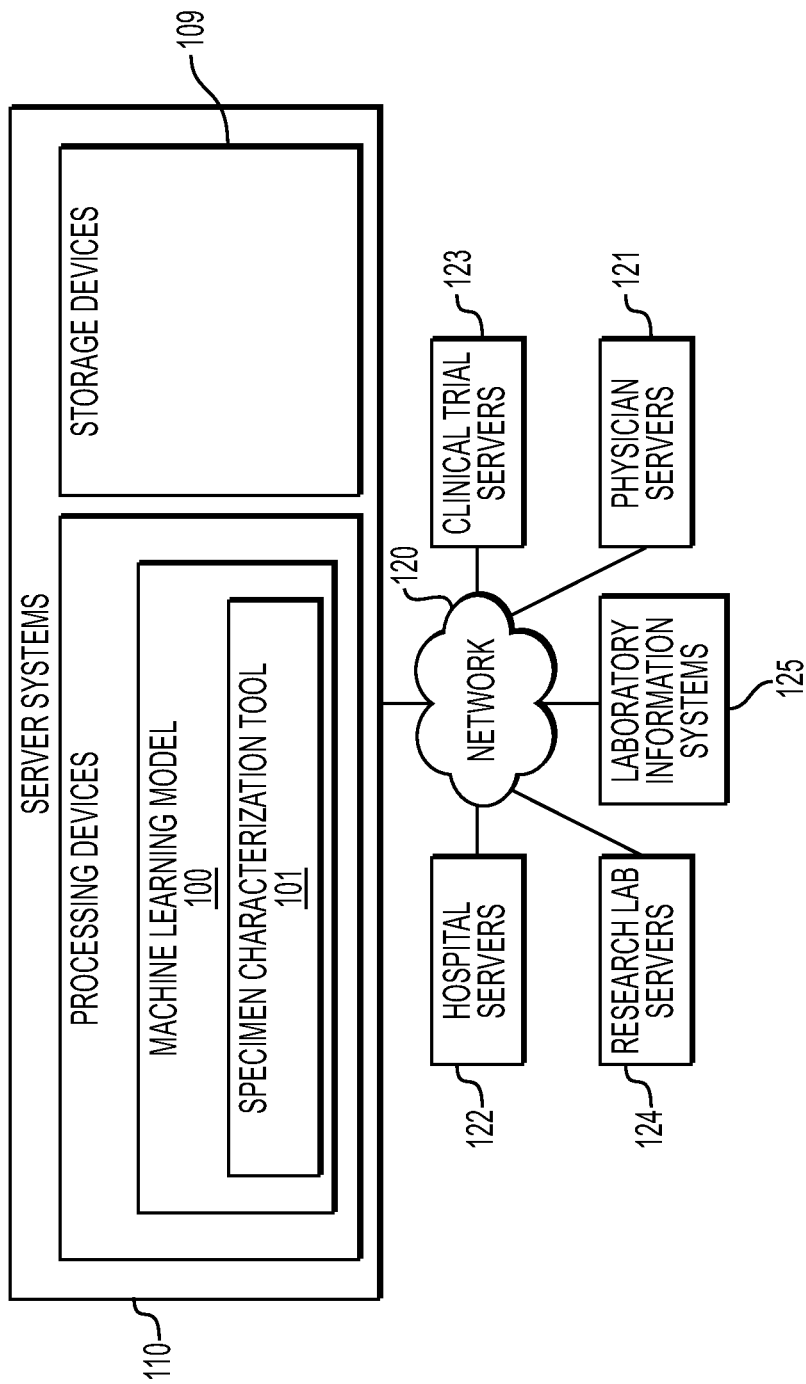
FIG. 1A illustrates an exemplary block diagram of a system and network for determining one or more characteristics based on pathology image(s), according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts. As used herein, the term "exemplary" is used in the sense of "example," rather than "ideal." Moreover, the terms "a" and "an" herein do not denote a limitation of quantity, but rather denote the presence of one or more of the referenced items. In the discussion that follows, relative terms such as "about," "substantially," "approximately," etc. are used to indicate a possible variation of ±10% or less in a stated value, numeric or otherwise.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a consolidated workflow for improving diagnosis of cancer and other diseases. The workflow may integrate, for example, slide evaluation, tasks, image analysis and cancer detection artificial intelligence (AI), annotations, consultations, and recommendations in one workstation. In particular, the present disclosure describes various exemplary AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. As described herein, this analysis may be done for specialized tasks such as clinical trials or for patients that potentially have a rare disease, making it harder to use AI technology to facilitate the analysis. Thus, the process of obtaining additional stained slides and tests may be done automatically before being reviewed by a pathologist. When paired with automatic slide segmenting and staining machines and a specialized machine learning model, this may provide a fully automated slide preparation pipeline. This automation has, at least, the benefits of (1) minimizing an amount of time wasted by a pathologist determining the findings of a slide by using an ineffective machine learning model (e.g., due to overcorrection), (2) minimizing the (average total) time from specimen acquisition to diagnosis by avoiding the additional time conducting manual analysis or questionable machine learning analysis, (3) reducing the amount of tissue material wasted/discarded during manual repeated slide preparation, (4) reducing the cost of slide preparation by partially or fully automating the procedure, (5) allowing higher volumes of slides to be generated per tissue block such that they are analyzed at the same time by a specialized machine learning model, contributing to more informed/precise diagnoses by reducing the overhead of requesting additional testing for a pathologist, and/or (6) identifying or verifying correct properties (e.g., pertaining to a specimen type) of a digital pathology image, etc.

The process of using computers to assist pathologists is called computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes using machine learning models and devices may be used to assist pathologists in detecting abnormalities that may otherwise be difficult to detect. For example, AI may be used to predict biomarkers (such as the over-expression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

The detected biomarkers by a specialized machine learning model could then be used to recommend specific cancer drugs or drug combination therapies to be used to treat a patient, and the AI could identify which drugs or drug combinations are unlikely to be successful by correlating the detected biomarkers with a database of treatment options. This can be used to facilitate the automatic recommendation of immunotherapy drugs to target a patient's specific cancer. Further, this could be used for enabling personalized cancer treatment for specific subsets of patients and/or rarer cancer types.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The AI and machine learning techniques described above may be applied to implementations where a limited training dataset is available. The limited training dataset may correspond to a small study, a clinical trial, and/or a rare disease such that the amount of training data available is not sufficient to train a non-initiated machine learning model as doing so would result in overfitting and, as a result, would result in the model making inaccurate predictions. According to implementations of the disclosed subject matter, the limitations of a small dataset may be mitigated by using a generalized machine learning model (e.g., a pan-cancer detection model) that is configured to learn tumor characteristics, morphology, and tumor microenvironments across cross tissue types. The generalized machine learning model may be trained based on a plurality different cancer types and based on a plurality of different inputs including histologist, genomic inputs, radiology images, lab tests, patient characteristics, and the like, or a combination thereof. The generalized machine learning model may be used to train a specialized machine learning model that is better suited to make predictions for a specialized task, such as a small study, clinical trial, or for a rare disease, where a small set of data is available.

The generalized machine learning model may be trained based on a first set of images and other inputs such that it is configured to receive patient specific inputs and output a cancer characteristic. The cancer characteristic may be a cancer diagnosis, tumor characterization, biomarker detection, or the like.

The generalized machine learning model may be optimized to generate a specialized machine learning model, using low-shot learning techniques. The low-shot learning techniques may be used to modify the generalized machine learning model to develop specialized biomarkers, drug response predictions, and/or cancer outcome predictions for smaller datasets. The smaller datasets may be, for example, from small studies, clinical trials, or for rare diseases where it may be impossible or difficult to conduct large-scale clinical trials to collect sufficient training data. Accordingly, the disclosed subject matter leverages a generalized cancer machine learning model that uses tumor characteristics, morphology and microenvironment for development of biomarkers in clinical and preclinical studies.

As further disclosed herein, digital images of pathology specimens (e.g., histology, cytology, immunohistochemistry, etc., or a combination thereof) and any associated information (e.g., genomic, lab tests, radiology, patient characteristics, etc.) may be received and stored. Each pathology specimen may be linked to the associated information as well as disease information about a respective disease presence, outcome status (response, recurrence, etc.), and/or the presence of any biomarkers.

A generalized machine learning model may be instantiated using deep learning and may be trained using a large amount (e.g., over 5,000, over 10,000, over 100,000, over 1,000,000, etc.) of the pathology specimens that are linked to the associated information as well the disease information. The generalized machine learning model may be trained to predict disease, biomarkers, and/or other attributes relevant to cancer diagnosis and treatment from multiple tissue types. Based on the training, the generalized machine learning model may detect the presence of cancer and/or biomarkers across a wide array of different tissue types such that the layers of the generalized machine learning model are tuned to identify tumor characteristics as well as normal and abnormal tissue morphology. The generalized machine learning model may be used to extract diagnostic features that can be used with a downstream machine learning algorithm or it can be fine-tuned for new tasks.

A specialized machine learning model may be generated for application with a small study (e.g., under 1000 samples, under 3,000 samples, under 4,000 samples, under 5000 samples, etc.) such as a clinical trial (e.g., phase 1, phase 2, phase 3), and/or a study for a rare disease where larger data samples cannot be obtained or are difficult to obtain. The specialized machine learning model may be generated by modifying the generalized machine learning model based on a specialized training dataset that is different than the training data set that the generalized machine learning model was trained on. The specialized training dataset may be from the small study or otherwise related to a specialized task with small data sets. The generalized machine learning model may be modified to generate the specialized machine learning model such that the specified machine learning model may leverage one or more layers of the generalized machine learning model and tune or replace one or more other layers to adapt to attributes of the small study. More specifically, the specialized machine learning model may leverage the cancer detection, tumor characterization, and/or biomarker detection capabilities of generalized machine learning model to build a specialized model configured for the small study.

FIG. 1A illustrates a block diagram of a system and network for determining specimen property or image property information pertaining to digital pathology image(s), using machine learning, according to an exemplary embodiment of the present disclosure. As further disclosed herein, the system and network of FIG. 1A may be used with a generalized machine learning model or a specialized machine learning model.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an implementation, the electronic network 120 may also be connected to server systems 110, which may include processing devices that are configured to implement a machine learning model 100, in accordance with an exemplary embodiment of the disclosed subject matter.

The physician servers 121, hospital servers 122, clinical trial servers 123, research lab servers 124, and/or laboratory information systems 125 may create or otherwise obtain images of one or more categories of pathology specimens including patients' cytology specimen(s), histopathology specimen(s), slide(s) of the cytology specimen(s), histology, immunohistochemistry, digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities via the machine learning model 100. For example, the processing devices may include a generalized machine learning model or a specialized machine learning model, as shown as machine learning model 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a LIS 125.

Figure 1B:
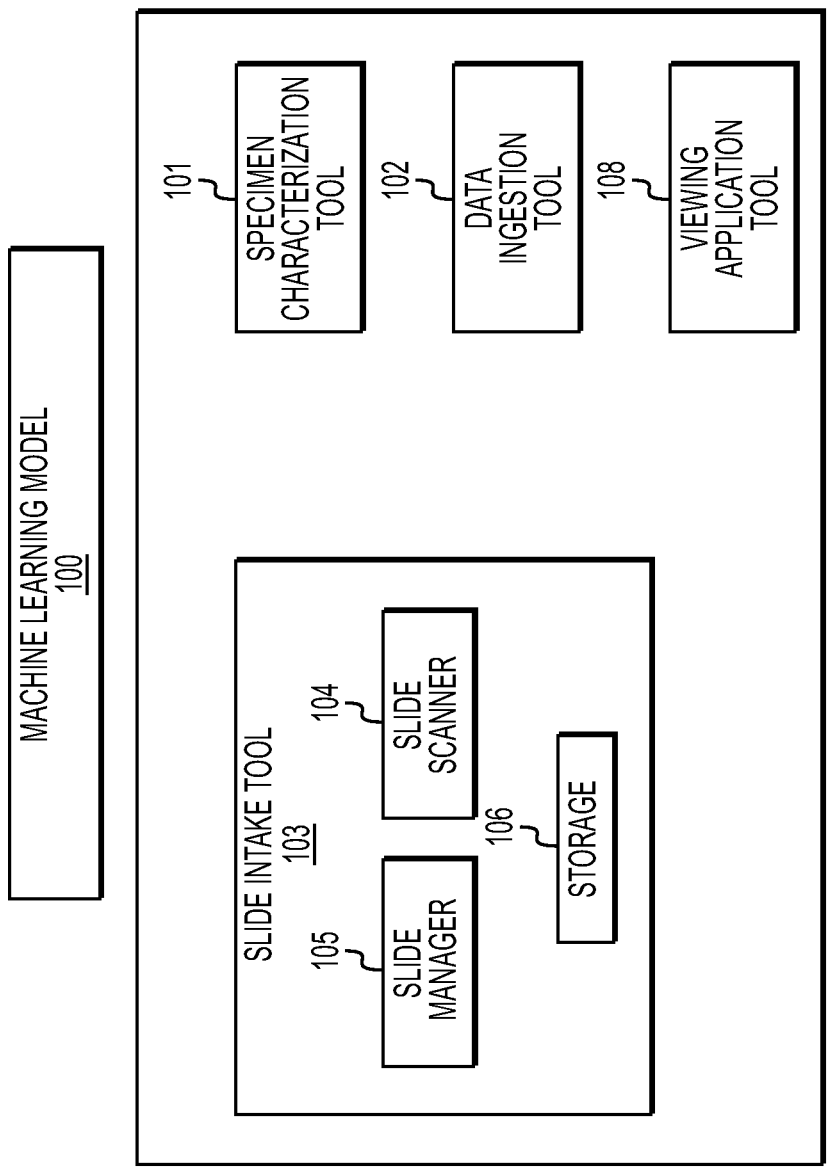
FIG. 1B illustrates an exemplary block diagram of a machine learning model, according to an exemplary embodiment of the present disclosure.

FIG. 1B illustrates an exemplary block diagram of a machine learning model 100 for determining specimen property or image property information pertaining to digital pathology image(s), using machine learning.

Specifically, FIG. 1B depicts components of the machine learning model 100, according to one embodiment. For example, the machine learning model 100 may include a specimen characterization tool 101, a data ingestion tool 102, a slide intake tool 103, a slide scanner 104, a slide manager 105, a storage 106, and a viewing application tool 108. For clarification, the machine learning model 100 shown in FIGS. 1A and 1B is a previously trained and generated machine learning model (e.g., a generalized machine learning model, specialized machine learning model, etc.). Additional disclosure is provided herein for training and generating different types of machine learning models that may be used as machine learning model 100.

The specimen characterization tool 101, as described herein, refers to a process and system for determining a characteristic (e.g., cancer characteristic) such as a specimen property or image property pertaining to digital pathology image(s) using a machine learning model such as the generalized machine learning model or the specialized machine learning model.

The data ingestion tool 102 refers to a process and system for facilitating a transfer of the digital pathology images to the various tools, modules, components, and devices of the machine learning model 100 that are used for characterizing and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with a characterization or image property information pertaining to digital pathology image(s), according to an exemplary embodiment. The information may be provided through various output interfaces (e.g., a screen, a monitor, a storage device, and/or a web browser, etc.). As an example, the viewing application tool 108 may apply an overlay layer over the digital pathology image(s) and the overlay layer may highlight key areas of consideration. The overlay layer may be or may be based on the output of the specimen characterization tool 101 of the machine learning model 100.

The specimen characterization tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the Specimen characterization tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

The specimen characterization tool 101 may provide the output of the machine learning model 100 (e.g., a generalized machine learning model, a specialized machine learning model, etc.). As an example, the slide intake tool 103 and the data ingestion tool 102 may receive inputs to the generalized machine learning model or a specialized machine learning model and the specimen characterization tool may identify biomarkers in the slides based on the data, and output an image highlighting the biomarkers via the viewing application tool 108.

Any of the above devices, tools, and modules may be located on a device that may be connected to an electronic network 120, such as the Internet or a cloud service provider, through one or more computers, servers, and/or handheld mobile devices.

Figure 2:
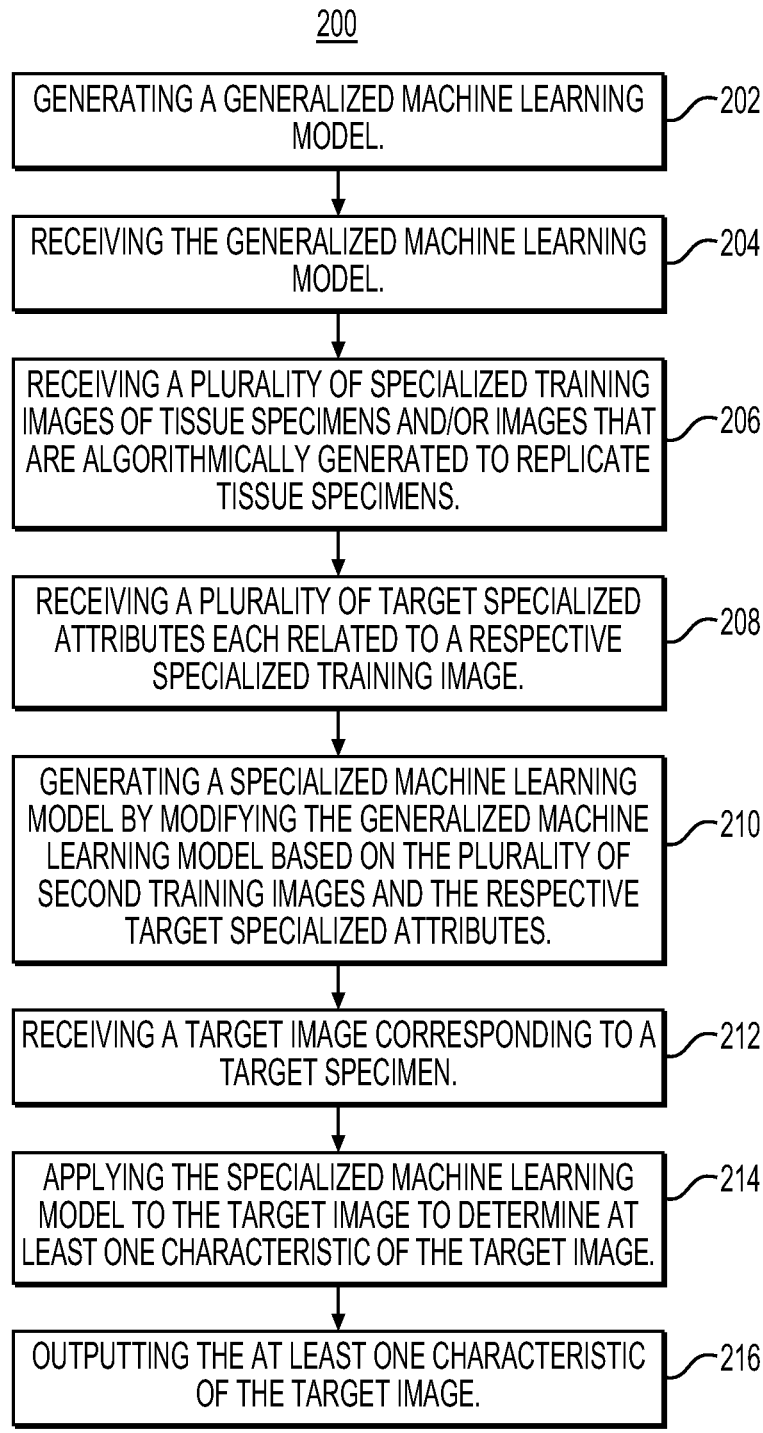
FIG. 2 is a flowchart illustrating an exemplary method for generating a specialized machine learning model to output characteristics of target images, according to an exemplary embodiment of the present disclosure.

FIG. 2 shows a flowchart 200 for outputting at least one characteristic of a specialized target image, in accordance with exemplary implementations of the disclosed subject matter. At 202 of FIG. 2, a generalized machine learning model may be generated. The generalized machine learning model may be generated to predict at least one cancer characteristic such as a diagnosis, a tissue characterization, a biomarker detection or the like. The generalized machine learning model may make predictions (e.g., biomarker detection) for different cancer types based on images of tissue specimens such as human tissue, animal tissue, or any applicable tissue and/or images that are algorithmically generated to replicate human tissue, animal tissue or any other applicable tissue. Tissue specimens may be from a single tissue specimen or multiple tissue specimen. At 204, the generalized machine learning model may be received, determined, and/or located at a training module such as training module 300 of FIG. 3, as further disclosed herein. At 206, a plurality of specialized training images of human tissue, animal tissue, or any applicable tissue and/or images that are algorithmically generated to replicate human tissue, animal tissue, or any applicable tissue, may be received. The plurality of specialized training images may correspond to a small study (e.g., clinical trial, rare disease, etc.) where only a limited amount of data is available. The specialized training images may all correspond to the same category of pathology specimens, as disclosed herein. At 208, a plurality of target specialized attributes each related to a respective specialized training image may be received. The attributes may be related to the respective patients based on whom the specialized training images are generated, may be based on the respective procedures, respective treatments, and/or other respective attributes. At 210, a specialized machine learning model may be generated by modifying the generalized machine learning model based on the plurality of specialized images received at 206 and the target specialized attributes received at 208. The specialized machine learning model generated at 210 may correspond to the machine learning model 100 of FIG. 1A.

A target image to be analyzed using the specialized machine learning model is received at 212. The target image may correspond to an image to be analyzed based on the specialized training dataset represented by the plurality of specialized training images received at 206. At 214, the specialized machine learning model may be applied to the target image to determine at least one characteristic of the target image. The at least one characteristic of the target image may be outputted via, for example, a report, a display, or any other applicable output, as further discussed herein.

The generalized machine learning model generated at 202 of FIG. 2 may be an end-to-end machine learning module, which may be instantiated using deep learning. The generalized machine learning model may detect the presence or absence of cancer across more than one tissue type (e.g., prostate cancer, breast cancer, bladder cancer, etc.). It may also detect additional biomarkers or information important for staging. For example, for bladder cancer, the generalized machine learning model may output the presence or absence of muscularis propria, a muscle that needs to be detected for bladder cancer staging. The generalized machine learning model may be trained with large amounts of data to predict disease, biomarkers, and other attributes relevant to cancer treatment from multiple tissue types. Through this process, it may detect the presence of cancer and/or biomarkers across a wide array of different tissue types such that its layers are built upon an understanding of tumor characteristics as well as normal and abnormal tissue morphology. The generalized machine learning model may be used to extract diagnostic features that can be used with a downstream machine learning algorithm or it can be "fine-tuned" for new tasks, as further disclosed herein.

To generate the generalized machine learning model at 202, a patient dataset including a large plurality of digital images of pathology specimens (e.g., histology, cytology, immunohistochemistry, etc.) may be received. The pathology specimens may be digital images generated based on physical biopsy samples, as disclosed herein, or may be images that are algorithmically generated to replicate human tissue, animal tissue, or any applicable tissue, by, for example, a rendering system or a generative adversarial model. Patient associated information (genomic information, lab tests, radiology, patient characteristics, patient information, treatment information, etc.) may also be received as part of the patient dataset. Additionally, as part of training the machine learning model, each patient dataset may be paired with information or indications about a cancer characteristic outputs (e.g., biomarkers) such as disease presence/absence, presence of staging variables (e.g., muscularis propria for bladder cancer), classification of the form of cancer (e.g., lobular or ductal for breast cancer), and other relevant variables for different cancer types, outcome status (e.g., response, recurrence, etc.) and/or the presence of any biomarkers.

The patient dataset, patient associated information, and/or the cancer characteristic outputs may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The generalized machine learning model may be generated based on applying the patient dataset and the patient associated information paired with the cancer characteristic output to a machine learning algorithm. The machine learning algorithm may accept, as inputs, the pathology specimens, the patient associated information, and the cancer characteristic outputs and implement training using one or more techniques. For example, the generalized machine learning model may be trained in one or more Convolutional Neural Networks (CNN), CNN with multiple-instance learning or multi-label multiple instance learning, Recurrent Neural Networks (RNN), Long-short term memory RNN (LSTM), Gated Recurrent Unit RNN (GRU), graph convolution networks, or the like or a combination thereof. Convolutional neural networks can directly learn the image feature representations necessary for discriminating among characteristics, which can work extremely well when there are large amounts of data to train on for each specimen, whereas the other methods can be used with either traditional computer vision features, e.g., SURF or SIFT, or with learned embeddings (e.g., descriptors) produced by a trained convolutional neural network, which can yield advantages when there are only small amounts of data to train on. The trained machine learning model may be configured to provide cancer characteristics as outputs based on patient data and patient associated information.

The generalized machine learning model may receive a patient dataset (e.g., one or more digital images of pathology specimen (e.g., histology, cytology, immunohistochemistry etc.)) as well as patient associated information (genomic, lab tests, radiology, patient characteristics etc.). The generalized machine learning model's trained algorithm may be applied to the patient dataset and the patient associated information to determine one or more cancer characteristics such as one or more regions of cancer in the digital images. The cancer characteristics may not be cancer specific such that the generalized machine learning model may provide cancer characteristics across cancer types, if any. The cancer characteristics may be spatially varying across one or more digital slides.

The output of the generalized machine learning model (i.e., the one or more cancer characteristics, if any) may be provided to a storage component (e.g., cloud storage, hard drive, network drive, etc.). If a spatially varying determination is made, the corresponding cancer characteristic(s) may be provided for digital display as for example, coordinates, bitmasks, overlays, or the like or a combination thereof.

Figure 3:
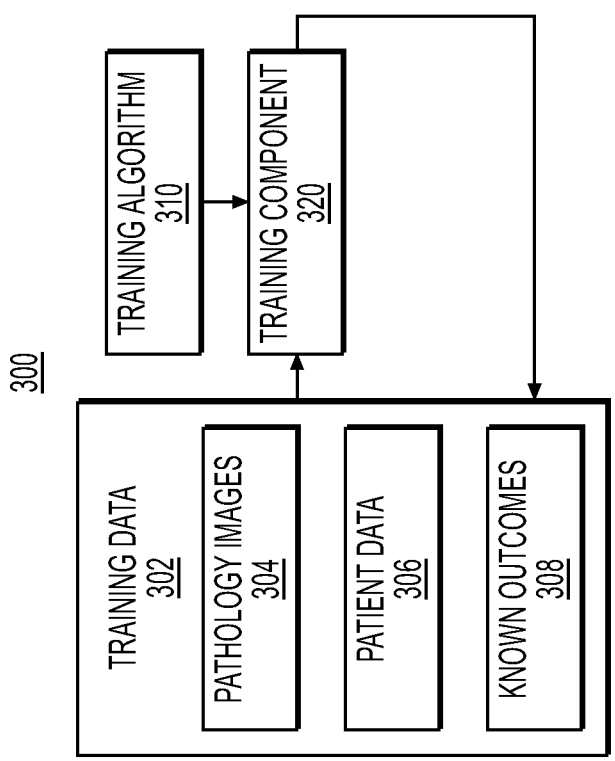
FIG. 3 illustrates an exemplary block diagram of a training module, according to an exemplary embodiment of the present disclosure.

FIG. 3 shows an example training module 300 to train either the generalized machine learning model or a specialized machine learning model, as further disclosed herein. As shown in FIG. 3, training data 302 may include one or more of pathology images 304 (e.g., digital representation of biopsied images), patient data 306 (e.g., a patient dataset), and known outcomes 308 (e.g., cancer characteristics) related to the patient data 306. The training data 302 and a training algorithm 310 may be provided to a training component 320 that may apply the training data 302 to the training algorithm 310 in order to generate a machine learning model.

At 206 of FIG. 2, a plurality of target specialized training images of human tissue, animal tissue, or any applicable tissue and/or images that are algorithmically generated to replicate human tissue, animal tissue, or any applicable tissue may be provided. The target specialized training images may correspond to images that are generated in a small study and may be directed to a specific cancer based implementation. The pathology specimens may be digital images generated based on physical biopsy samples, as disclosed herein, or may be images that are algorithmically generated to replicate human tissue, animal tissue, or any applicable tissue by, for example, a rendering system or a generative adversarial model.

The target specialized training images for a target specialized task (e.g., corresponding to a rare disease, a small study, a clinical study, etc.) may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of such digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

Compared to the images received as part of the training dataset of the generalized machine learning model, the number of target specialized training images for training a specialized machine learning model may be substantially lower (e.g., by one or two magnitudes). The lower number of target specialized training images may be a result of the target specialized training images corresponding to the target specialized task for a small study, clinical study, or a rare disease where an larger number of training data is not available.

At 208, a plurality of target specialized attributes related to a respective specialized training image may be received. The target specialized attributes may be paired with the training image and may include patient associated information (genomic information, lab tests, radiology, patient characteristics, patient information, treatment information, etc.). Additionally, the target specialized attributes may include information or indications about a cancer characteristic outputs (e.g., biomarkers) such as disease presence/absence, presence of staging variables, drug response, toxicity, classification of the form of cancer, and other relevant variables for different cancer types, outcome status and/or the presence of any biomarkers.

At 210 of FIG. 2, a specialized machine learning model may be generated for a target specialized task. The specialized machine learning model may be generated by modifying the generalized machine learning model by first modifying the generalized machine learning model to have the appropriate outputs for the target specialized task. A generalized machine learning model may be trained utilizing data associated with various cancer types and other output targets (e.g., severity of cancer, mutations present, etc.). The generalized machine learning model may be able to recognize tumor regions/characteristics for different types of cancer types without specifically providing a cancer type that a corresponding tissue is associated with. Such an ability to recognize regions/characteristics for different types of cancer provides the generalized machine learning model with internal representations (e.g., parameters, layers, weights associated with layers, relationships, etc.) that work effectively for other tasks where there is less data. According an implementation, a biomarker detection system (e.g., specialized machine learning model) is initialized with the generalized machine learning model's parameters and, for example, the output layer, if implemented in a form of neural network, is re-initialized to be fine-tuned to infer the biomarker task. The fine-tuning training can then be done with gradient descent. Optionally, this process can be constrained by only training the last M layers of the network or using methods such as L2-SP to limit the ability for the network to overfit. Additionally, specialized machine learning model may be generated by modifying the generalized machine learning model using the plurality of specialized training images of 206 and the plurality of target specialized attributes of 208. The generalized machine learning model may be modified to have the appropriate outputs for the biomarker detection task. Additionally or alternatively, the generalized machine learning model may be modified to extract features from samples for use with the specialized machine learning model.

The specialized machine learning model may be generated using a small amount of data by modifying the generalized machine learning model by fine-tuning (e.g., re-training) one or more layers of the generalized machine learning model using the specialized task and related material (e.g., specialized training images, target specialized attributes, etc.). The fine-tuning may be conducted using L2-SP, Deep Learning Transfer (DELTA) (e.g., using a feature map), and/or one or more other approaches designed to improve generalization. Alternatively or in addition, the specialized machine learning model may be generated using large-margin methods built on top of the generalized machine learning model to improve generalization. Alternatively or in addition, the specialized machine learning model may be generated using methods for low-shot learning. Alternatively or in addition, the specialized machine learning model may be generated using the generalized machine learning model to extract features and then training a model based on those features (e.g., nearest neighbor, random forest, support vector machine, neural network, etc.).

The specialized machine learning model may be generated by performing transfer learning in deep learning using the generalized machine learning model. Transfer learning may be used to accelerate the training of the specialized machine learning model as either a weight initialization scheme or feature extraction method. The weights of the generalize machine learning model pre-trained by the training dataset with a sufficiently large number of instances may provide a better initialization for the target specialized task based specialized machine learning model, than a random initializations.

According to a weight initialization scheme, the weights in lower convolution layers may be fixed and weights in upper layers may re-trained using data from the target task and its related material (e.g., specialized training images, target specialized attributes, etc.). The weights in re-used layers may be used as the starting point for the training process and adapted in response to the target task. This weight initialization scheme may treat transfer learning as a type of weight initialization scheme.

Alternately, in accordance with a feature extraction scheme, the weights of the generalized machine learning network may not be adapted when training the specialized machine learning network, in response to the target task, such that only new layers after the reused layers may be trained to interpret their output.

Accordingly, the generalized machine learning model and the specialized machine learning model may share one or more layers and may have at least one layer that is different than each other. As an example, the output layer of the generalized machine learning model may be modified at 210 of FIG. 2 such that a target image received as an input at the specialized machine learning model provides a different result than if the same target image was received as an input at the generalized machine learning model.

At 210 of FIG. 2, the specialized machine learning model may be trained using a training module 300 of FIG. 3 in a manner similar to that described herein for training the generalized machine learning model. As shown in FIG. 3, training data 302 may include one or more of pathology images 304 (e.g., digital representation of biopsied images), patient data 306 (e.g., a patient dataset), and known outcomes 308 (e.g., cancer characteristics) related to the patient data 306. The pathology images 304 may include the specialized training images of 206 of FIG. 2. The known outcomes 308 may include the target specialized attributes of 208 of FIG. 2. The training data 302 and a training algorithm 310 may be provided to a training component 320 that may apply the training data 302 to the training algorithm 310 in order to generate a specialized machine learning model.

Figure 4:
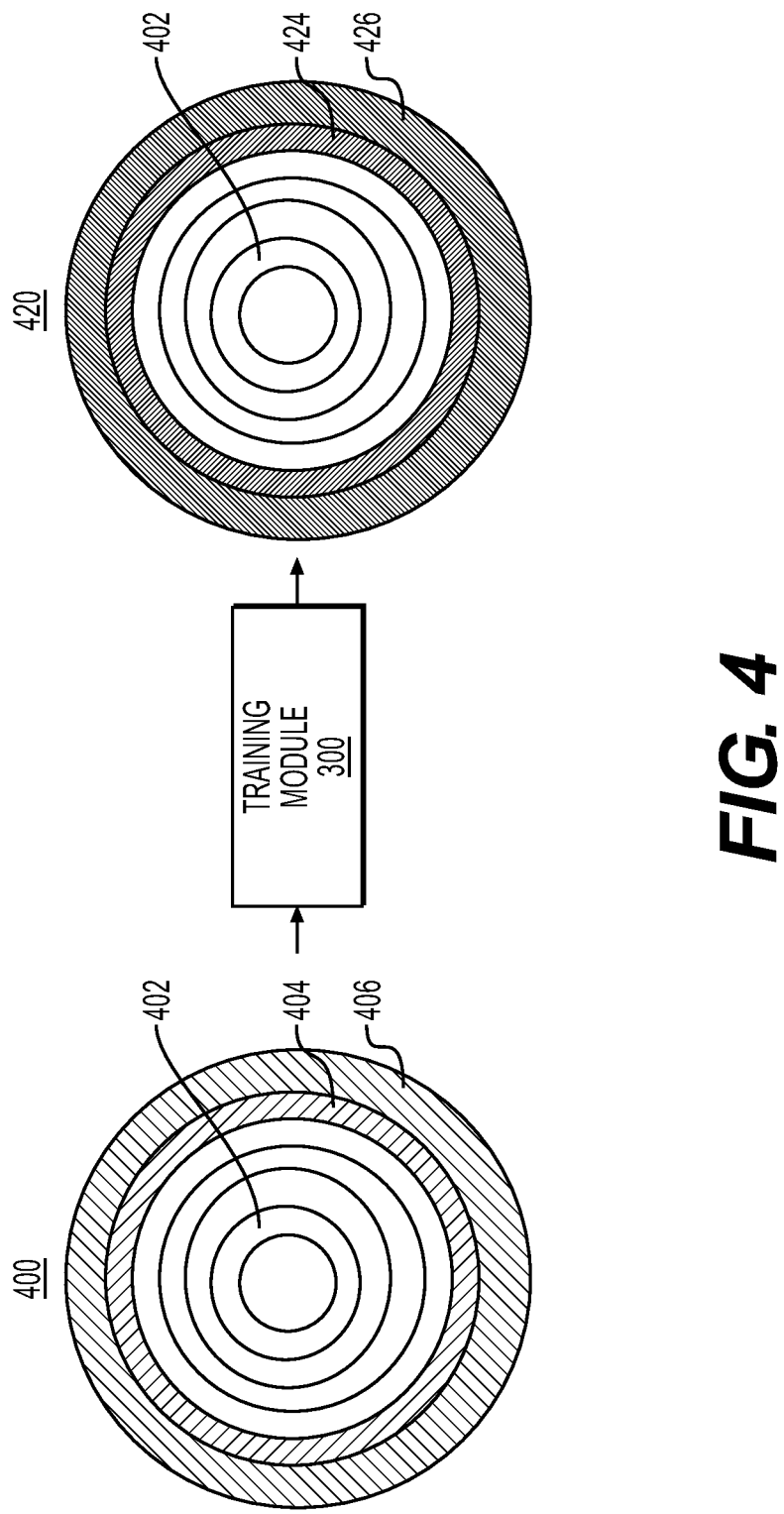
FIG. 4 illustrates a diagram of a generalized machine learning model and a specialized machine learning model, according to an exemplary embodiment of the present disclosure.

FIG. 4 is a diagram that shows a generalized machine learning model 400 and a specialized machine learning model 420. The generalized machine learning model may have a number of inner layers 402 as well as a first outer layer 404 and a second outer layer 406. According to an example, an outer layer may be a layer that is formed later in the training of a machine learning model in comparison to an inner layer. According to another example, an outer layer may be more specific compared to an inner layer that is more general. The generalized machine learning model 400 may be generated using a large amount of training data to output cancer characteristics across different cancer types, as disclosed herein. The generalized machine learning model 400 may be provided to training module 300 along with the specialized training images of 206 and target specialized attributes 208 of FIG. 2.

The training module 300 may be configured to generate the specialized machine learning model 420 by maintaining the inner layers 402 of the generalized machine learning model and modifying the first outer layer 404 and second outer layer 406 to a first outer layer 424 and second outer layer 426. Training of the specialized machine learning model 420 may be initialized based on the inner layers 402 and the training module 300 may replace, modify, or tweak the first outer layer 404 and second outer layer 406 based on the specialized training images of 206 and target specialized attributes 208 of FIG. 2. Accordingly, the specialized machine learning model 420 may be trained using a relatively small amount of data and may leverage the previously trained inner layers 402 of the generalized machine learning model 400. As the generalized machine learning model 400 is trained to identify cancer characteristics, the inner layers 402 may be provide a more applicable initialization for the specialized machine learning model 420 than initializing the specialized machine learning model 420 without the inner layers 402.

It will be understood that although first outer layer 404 and second outer layer 406 are shown the be modified, the any number of layers less than the total number of layers in the generalized machine learning model 400 may be modified to generate the specialized machine learning model 420. As an example, the second outer layer 406 may be an output layer and only the output layer of the generalized machine learning model may be modified when generating the specialized machine learning model 420. Additionally, it will be understood that although the inner layers 402 of the generalized machine learning model 400 are maintained when training the specialized machine learning model 420, implementations of the disclosed subject matter are not limited to inner layers. Any applicable layers of the generalized machine learning model 400 may be maintained or modified/replaced to generate the specialized machine learning model 420.

The specialized machine learning model may be used to make predictions such as to determine one or more biomarkers across cancer types. The specialized machine learning model may determine the presence or absence of one or more biomarkers in one or more slide images. This determination may be spatially varying across a target image (e.g., a digital pathology slide) such that different tumors in different regions of the slides are determined to have the presence or absence of different biomarkers.

The machine learning model generated at 210 may be the same as or similar to the machine learning model 100 of FIG. 1A and may receive target images, and patient information from one or more of the physician servers 121, hospital servers 122, clinical trial servers 123, research lab servers 124, and/or laboratory information systems 125, etc. At 212, the target image corresponding to a target specimen may be received. At 214, the specialized machine learning model may be applied to the target image to determine at least one characteristic of the target image. The at least one characteristic may be a cancer characteristic associated with the target specialized task based on which the specialized machine learning model was generated. At 216, the at least one characteristic of the target image may be output via one or more output interfaces (e.g., a screen, a monitor, a storage device, and/or a web browser, etc.). The output characteristic may be a specimen type (e.g., cancer prediction, drug response, cancer reoccurrence rate, toxicity, tissue abnormality, etc.). Accordingly, the output at 216 may be the prediction of the specimen type based on the target image received at 212. As an example, the viewing application tool 108 of FIG. 1A may apply an overlay layer over the digital pathology image(s) and the overlay layer may highlight key areas of consideration. The output may be provided as coordinates, bitmasks, overlays, or the like or a combination thereof.

A specialized machine learning model may be used for a number of implementations such as, not limited to, drug response predictions for patient stratification in clinical trials, cancer recurrence predictions, drug toxicity or abnormality predictions, or the like.

Figure 5:
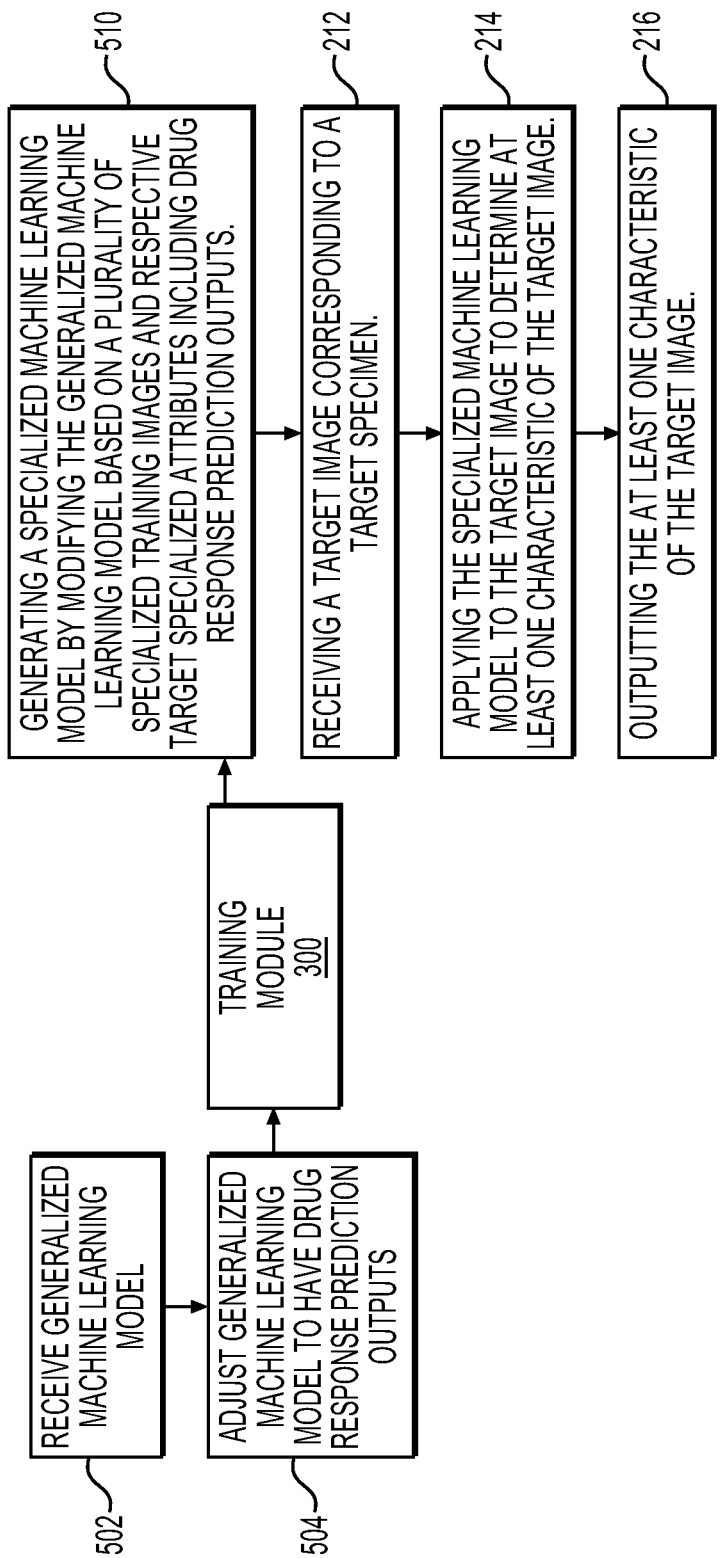
FIG. 5 is a flowchart of an exemplary embodiment of drug response predictions, according to an exemplary embodiment of the present disclosure.

FIG. 5 shows an example implementation of a specialized machine learning model, generated using a generalized machine model, for drug response predictions. Developing biomarkers for trial drugs is traditionally conducted through clinical studies where the sample size is typically under 5000 patients. With such small datasets, it is difficult to fully understand the underlying disease mechanism and to predict patient characteristics for a treatment. Techniques disclosed herein including a generalized machine learning model that fully characterizes tumors their morphology can be used as an initialization step for detecting biomarkers for identifying which patients will respond to a treatment in clinical trials, and what the response may be. As shown in FIG. 5, at 502, a generalized machine learning model may be received at 502. The generalized machine learning model may be adjusted to have drug response prediction outputs at 504. The adjustment may be made by adjusting the weights in one or more layers of the generalized machine learning model and/or the weights of the output layer of the generalized machine learning model, and/or modifying attributes of the outputs of the generalized machine learning model.

The adjusted machine learning model may be provided to training module 300. The training module 300 may be configured to generate the specialized machine learning model, at 510, by maintaining the one or more layers (e.g., inner layers) of the generalized machine learning model and modifying one or more layers (e.g., the outer layers) of the machine learning model. The specialized machine learning model may be trained using a relatively small amount of data and may leverage the previously trained layers of the generalized machine learning model. The specialized machine learning model may be trained by providing pathology images and corresponding patient data for patients that were provided a target drug. Additionally, known outcomes of the target drug may also be provided to the training module 300 to train the specialized machine learning model.

At 510, the specialized machine learning model may be generated based on modifying the generalized machine learning model received at 520 and training based on specialized training images from patients that are provided the target drug, as well as their known responses to the drug. The specialized machine learning model generated at 510 may be used to predict drug response outcomes based on one more target images. FIG. 5 shows steps 212, 214, and 216 of FIG. 2 and disclosure related to these steps is not repeated here for brevity. At 212, a target image corresponding to a target specimen may be received. At 214, the specialized machine learning model generated at 510 may be applied to the target image to determine a characteristic of the target image. In the implementation provided in FIG. 5, the characteristic of the target image may be the response (e.g., positive, negative, neutral, predict issues, etc.) that the patient from whom the target image was captured may have to the target drug. At 216, the characteristic may be output in accordance with the disclosure provided herein.

Figure 6:
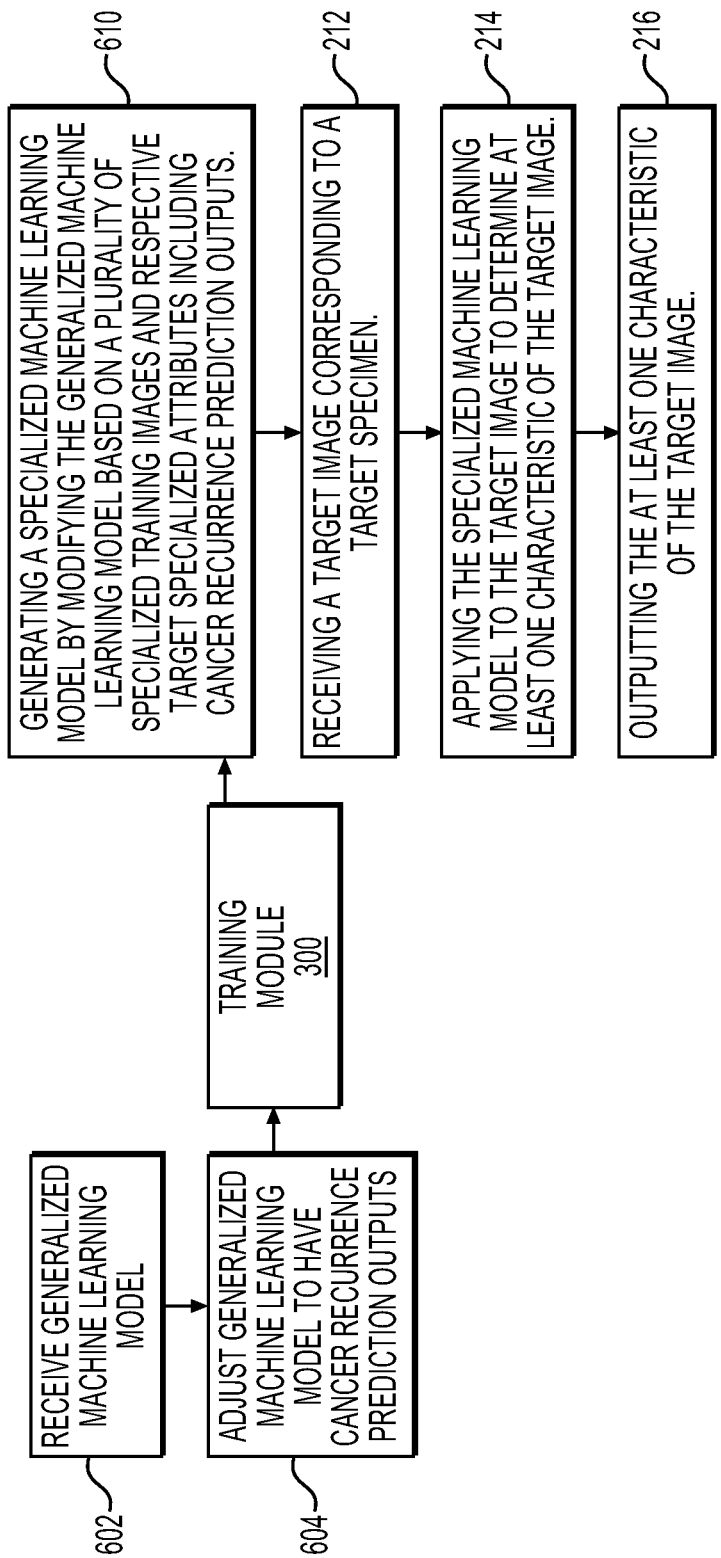
FIG. 6 is a flowchart of an exemplary embodiment of cancer recurrence predictions, according to an exemplary embodiment of the present disclosure.
Figure 7:
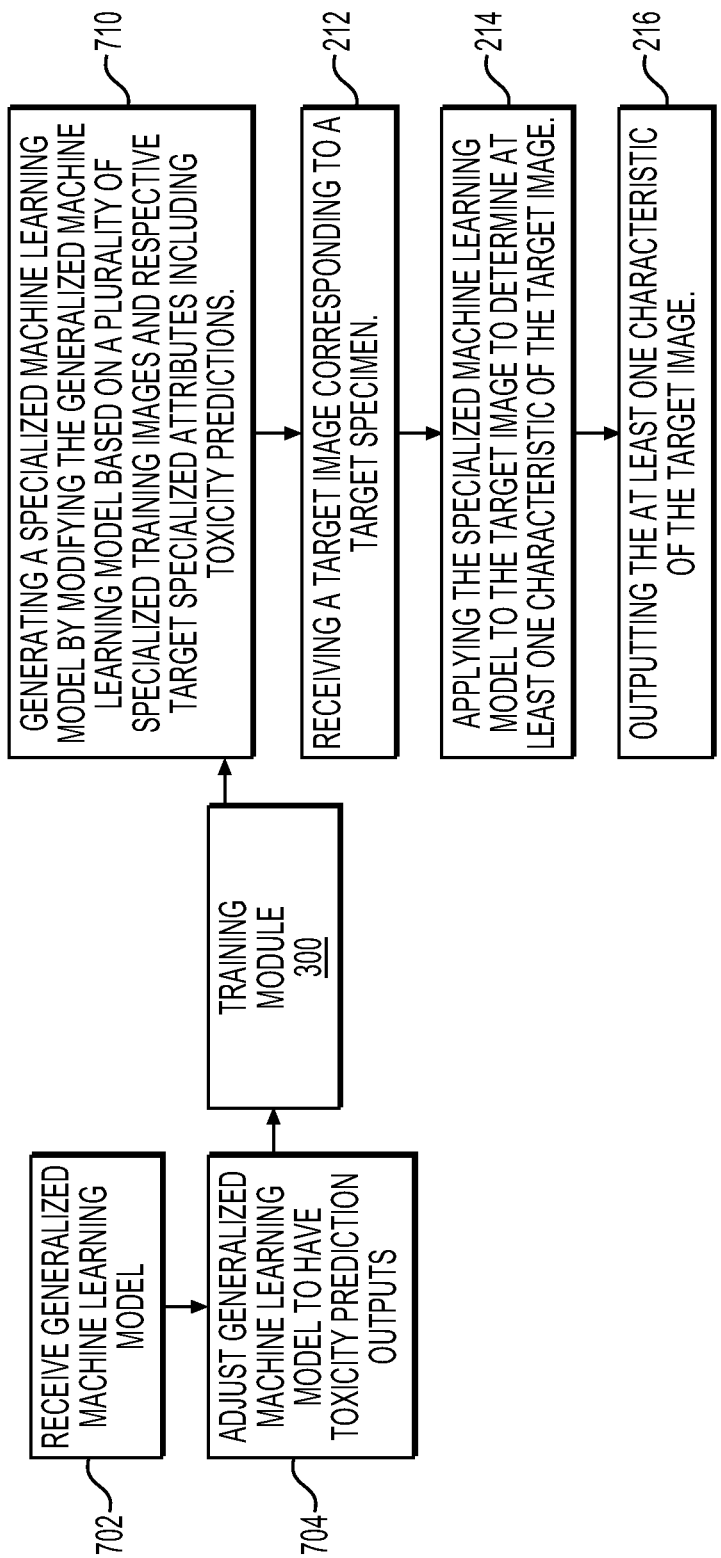
FIG. 7 is a flowchart of an exemplary embodiment of drug toxicity and tissue abnormality predictions, according to an exemplary embodiment of the present disclosure.

According to an implementation, the generalized machine learning model received in the example implementations provided in FIG. 5 (i.e., at 502), FIG. 6 (i.e., at 602), and FIG. 7 (i.e., at 702), may be the same generalized machine learning model. Each of the respective specialized machine learning models generated at 510, 610, and 710 may be initialized using all or some of the layers from the generalized machine learning model. However, each of the respective specialized machine learning models generated at 510, 610, and 710 may be different such that they tuned to each of their specific specialized tasks. Accordingly, a given input image provided to each of the specialized machine learning models generated at 510, 610, and 710 may result in different outputs, based on the differences between the specialized machine learning models generated at 510, 610, and 710.

FIG. 6 shows an example implementation of a specialized machine learning model, generated using a generalized machine model, for cancer recurrence predictions. Recurrence of cancer may occur when cancer reoccurs after treatment (e.g., a successful or unsuccessful treatment). Knowing whether a cancer will recur may enable better treatment planning. For example, knowing a potential recurrence probability based on one or more given treatments (e.g., Immunotherapy, Chimeric antigen receptor T (CART-T) cell-based therapy, etc.), may enable customization or tailoring of the treatments for each patient. Additionally, newer treatment mechanisms may affect tumor's recurrence in later stages and knowing a probability associated with such late stage recurrences may help mitigate the recurrence rates. However, building a machine learning model to assess cancer recurrence directly from traditional studies is challenging due to limited number of datasets. Techniques disclosed herein including a generalized machine learning model that characterizes tumors their morphology can be used for initiating a specialized machine learning model for predicting cancer recurrence in studies with limited datasets. As shown in FIG. 6, at 602, a generalized machine learning model may be received at 602. The generalized machine learning model may be adjusted to have cancer recurrence prediction outputs at 604. The adjustment may be made by adjusting the weights in one or more layers of the generalized machine learning model and/or the weights of the output layer of the generalized machine learning model, and/or modifying attributes of the outputs of the generalized machine learning model.

The adjusted machine learning model may be provided to training module 300. The training module 300 may be configured to generate the specialized machine learning model, at 610, by maintaining the one or more layers (e.g., inner layers) of the generalized machine learning model and modifying one or more layers (e.g., the outer layers) of the machine learning model. The specialized machine learning model may be trained using a relatively small amount of data and may leverage the previously trained layers of the generalized machine learning model. The specialized machine learning model may be trained by providing pathology images and corresponding patient data for patients that either exhibited cancer recurrence or did not exhibit cancer recurrence. Additionally, the known outcomes of cancer recurrence or lack of recurrence may also be provided to the training module 300 to train the specialized machine learning model.

At 610, the specialized machine learning model may be generated based on modifying the generalized machine learning model received at 620 and training based on specialized training images from patients that exhibited or did not exhibit cancer recurrence, as well as their known responses to the drug. The specialized machine learning model generated at 610 may be used to predict cancer recurrence outcomes based on one more target images. FIG. 6 shows steps 212, 214, and 216 of FIG. 2 and disclosure related to these steps is not repeated here for brevity. At 212, a target image corresponding to a target specimen may be received. At 214, the specialized machine learning model generated at 610 may be applied to the target image to determine a characteristic of the target image. In the implementation provided in FIG. 6, the characteristic of the target image may be the probability that the patient from whom the target image was captured may exhibit cancer recurrence. Alternatively or in addition, the characteristic may be a degree of cancer recurrence that the patient from whom the target image was captured may exhibit. At 216, the characteristic may be output in accordance with the disclosure provided herein.

FIG. 7 shows an example implementation of a specialized machine learning model, generated using a generalized machine model, for drug toxicity or tissue abnormality prediction. In drug development cycle, potential compounds go through rounds of safety studies in animals and then humans. For example, based on current practices, assessment of toxicity is conducted manually via pathology testing in animal tissues. The number of animals in toxicity preclinical studies is quite limited and may require testing of multiple doses of a new molecular entity. Techniques disclosed herein including a generalized machine learning model that was trained on various human tissues, animal tissues, or any applicable tissues, that is weighted based on learned the tumor morphology can be used as an initialization step to detect abnormalities in tissues (e.g., animal tissues) when making predictions for preclinical toxicity studies. As shown in FIG. 7, at 702, a generalized machine learning model may be received at 702. The generalized machine learning model may be adjusted to have drug toxicity or tissue abnormality prediction outputs at 704. The adjustment may be made by adjusting the weights in one or more layers of the generalized machine learning model and/or the weights of the output layer of the generalized machine learning model, and/or modifying attributes of the outputs of the generalized machine learning model.

The adjusted machine learning model may be provided to training module 300. The training module 300 may be configured to generate the specialized machine learning model, at 710, by maintaining the one or more layers (e.g., inner layers) of the generalized machine learning model and modifying one or more layers (e.g., the outer layers) of the machine learning model. The specialized machine learning model may be trained using a relatively small amount of data and may leverage the previously trained layers of the generalized machine learning model. The specialized machine learning model may be trained by providing pathology images and corresponding patient data for patients (e.g., human and/or animal) that were provided a target drug. Additionally, known outcomes of the target drug's toxicity or resulting tissue abnormality may also be provided to the training module 300 to train the specialized machine learning model.

At 710, the specialized machine learning model may be generated based on modifying the generalized machine learning model received at 720 and training based on specialized training images from patients that are provided the target drug, as well as their known toxicity or tissue abnormality from the drug. The specialized machine learning model generated at 710 may be used to predict drug toxicity or tissue abnormality outcomes based on one more target images. FIG. 7 shows steps 212, 214, and 216 of FIG. 2 and disclosure related to these steps is not repeated here for brevity. At 212, a target image corresponding to a target specimen may be received. At 214, the specialized machine learning model generated at 710 may be applied to the target image to determine a characteristic of the target image. In the implementation provided in FIG. 7, the characteristic of the target image may be the presence or absence, or degree of toxicity or tissue abnormality that the patient from whom the target image was captured may have to the target drug. At 216, the characteristic may be output in accordance with the disclosure provided herein.

Figure 8:
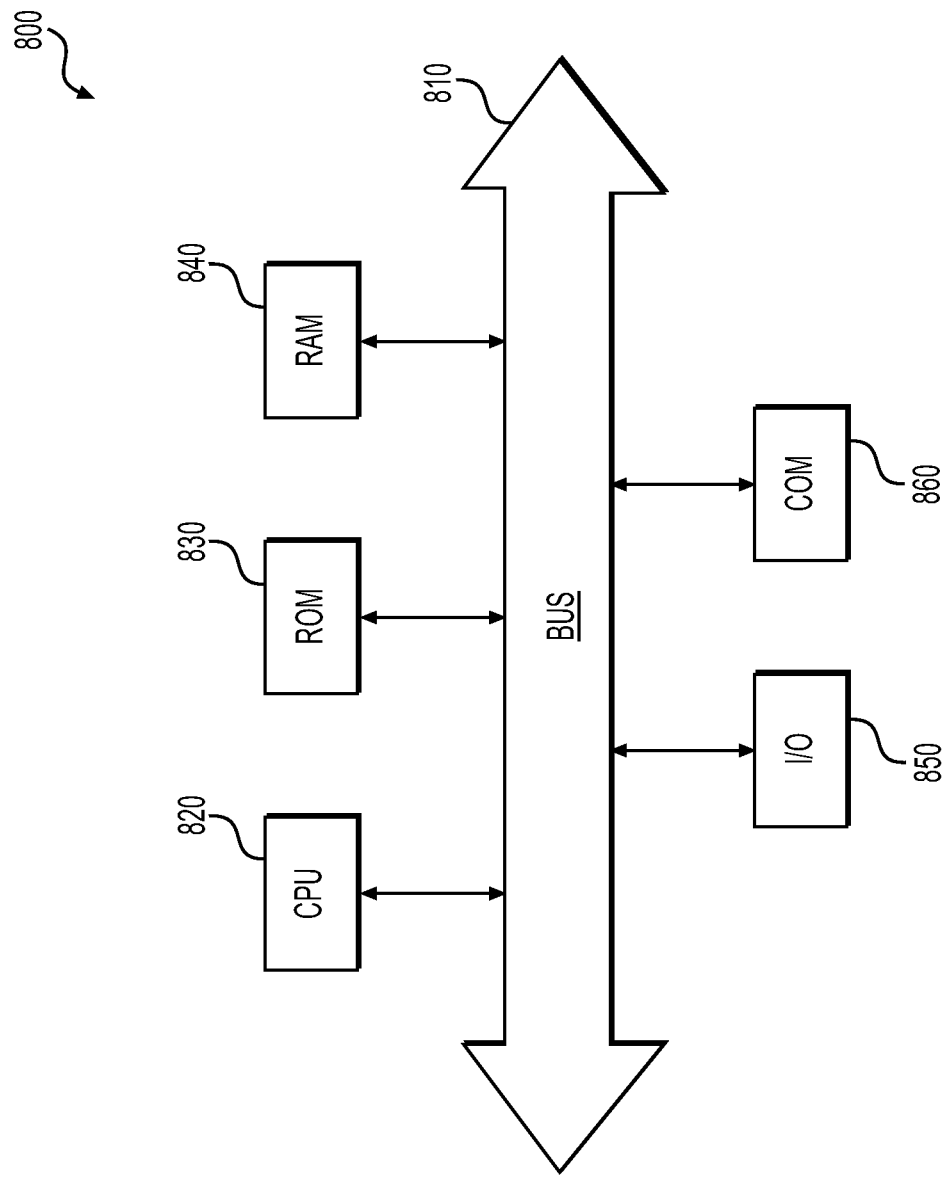
FIG. 8 depicts an example system that may execute techniques presented herein.

As shown in FIG. 8, device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multi-processor system, such system operating alone, or in a cluster of computing devices operating in a cluster or server farm. CPU 820 may be connected to a data communication infrastructure 810, for example, a bus, message queue, network, or multi-core message-passing scheme.

Device 800 also may include a main memory 840, for example, random access memory (RAM), and also may include a secondary memory 830. Secondary memory 830, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include other similar means for allowing computer programs or other instructions to be loaded into device 800. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical, or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 800 also may include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for processing electronic images, the method comprising:
receiving a generalized machine learning model generated by processing a plurality of first training images to predict at least one cancer characteristic;
receiving a plurality of second training images, wherein the first training images and the second training images comprise images of tissue specimens and/or images algorithmically generated to replicate tissue specimens, a quantity of second training images being insufficient to generate a machine learning model that meets a threshold for outputting one or more characteristics of target images for a specialized task;
receiving a plurality of target specialized attributes each related to a respective second training image of the plurality of second training images;
generating a specialized machine learning model by modifying the generalized machine learning model based on the plurality of second training images and respective target specialized attributes, the specialized machine learning model meeting the threshold for outputting the one or more characteristics of target images for the specialized task, the specialized machine learning model being generated in accordance with a feature extraction scheme by generating additional layers to an existing set of layers of the generalized machine learning model and generating weights for the additional layers based on the plurality of second training images and the target specialized attributes;
receiving a target image corresponding to a target specimen;
applying the specialized machine learning model to the target image to determine at least one characteristic of the target image; and
outputting the at least one characteristic of the target image.

2. The computer-implemented method of claim 1, further comprising:

determining a prediction of a specimen type of the target specimen based on the at least one characteristic of the target image; and outputting the prediction of the specimen type of the target specimen.

3. The computer-implemented method of claim 1, wherein the plurality of target specialized attributes are one or more biomarkers present within each respective second training image.

4. The computer-implemented method of claim 1, wherein the generalized machine learning model comprises a plurality of layers and modifying the generalized machine learning model further comprises modifying one or more outer layers of the generalized machine learning model.

5. The computer-implemented method of claim 1, wherein modifying the generalized machine learning model further comprises removing an output layer of the generalized machine learning model.

6. The computer-implemented method of claim 1, wherein the plurality of target specialized attributes are one or more indications of characteristic outputs selected from a disease presence, staging variable presence, drug response, toxicity, or cancer classification.

7. The computer-implemented method of claim 1, wherein the plurality of target specialized attributes are based on at least one of drug response information, cancer recurrence prediction information, or toxicity assessment information.

8. The computer-implemented method of claim 1, wherein each of second training images are generated based on a same category of pathology specimens.

9. The computer-implemented method of claim 8, wherein a category of pathology specimens is selected from histology, cytology, immunohistochemistry, or a combination thereof.

10. The computer-implemented method of claim 1, wherein modifying a generalized machine learning model further comprises adjusting the generalized machine learning model to have outputs based on the target specialized attributes.

11. The computer-implemented method of claim 1, wherein the plurality of first training images comprise images corresponding to a plurality of cancer types.

12. The computer-implemented method of claim 1, wherein the at least one cancer characteristic is one of a cancer diagnosis, a tumor characterization, or biomarker detection.

13. A system for processing electronic images, the system comprising:
at least one memory storing instructions; and
at least one processor executing the instructions to perform operations comprising:
receiving a generalized machine learning model generated by processing a plurality of first training images to predict at least one cancer characteristic;
receiving a plurality of second training images, wherein the first training images and the second training images comprise images of tissue specimens and/or images algorithmically generated to replicate tissue specimens a quantity of second training images being insufficient to generate a machine learning model that meets a threshold for outputting one or more characteristics of target images for a specialized task;
receiving a plurality of target specialized attributes each related to a respective second training image of the plurality of second training images;
generating a specialized machine learning model by modifying the generalized machine learning model based on the plurality of second training images and the respective target specialized attributes, the specialized machine learning model meeting the threshold for outputting the one or more characteristics of target images for the specialized task, the specialized machine learning model being generated in accordance with a feature extraction scheme by generating additional layers to an existing set of layers of the generalized machine learning model and generating weights for the additional layers based on the plurality of second training images and the target specialized attributes;
receiving a target image corresponding to a target specimen;
applying the specialized machine learning model to the target image to determine at least one characteristic of the target image; and
outputting the at least one characteristic of the target image.

14. The system of claim 13, the operations further comprising:
determining a prediction of a specimen type of the target specimen based on the at least one characteristic of the target image; and
outputting the prediction of the specimen type of the target specimen.

15. The system of claim 13, wherein the plurality of target specialized attributes are one or more biomarkers present within each respective second training image.

16. The system of claim 13, wherein the generalized machine learning model comprises a plurality of layers and modifying the generalized machine learning model further comprises modifying one or more outer layers of the generalized machine learning model.

17. The system of claim 13, wherein modifying the generalized machine learning model further comprises removing an output layer of the generalized machine learning model.

18. A non-transitory computer-readable medium storing instructions that, when executed by processor, cause the processor to perform operations for processing electronic images, the operations comprising:
receiving a generalized machine learning model generated by processing a plurality of first training images to predict at least one cancer characteristic;
receiving a plurality of second training images, wherein the first training images and the second training images comprise images of tissue specimens and/or images algorithmically generated to replicate tissue specimens a quantity of second training images being insufficient to generate a machine learning model that meets a threshold for outputting one or more characteristics of target images for a specialized task;
receiving a plurality of target specialized attributes each related to a respective second training image of the plurality of second training images;
generating a specialized machine learning model by modifying the generalized machine learning model based on the plurality of second training images and the respective target specialized attributes, the specialized machine learning model meeting the threshold for outputting the one or more characteristics of target images for the specialized task, the specialized machine learning model being generated in accordance with a feature extraction scheme by generating additional layers to an existing set of layers of the generalized machine learning model and generating weights for the additional layers based on the plurality of second training images and the target specialized attributes;

receiving a target image corresponding to a target specimen;

applying the specialized machine learning model to the target image to determine at least one characteristic of the target image; and outputting the at least one characteristic of the target image.

19. The non-transitory computer-readable medium of claim 18, the operations further comprising:

determining a prediction of a specimen type of the target specimen based on the at least one characteristic of the target image; and outputting the prediction of the specimen type of the target specimen.

20. The non-transitory computer-readable medium of claim 18, wherein the plurality of target specialized attributes are one or more biomarkers present within each respective second training image.

* * * * *